(12) United States Patent
Hendrick et al.

(10) Patent No.: US 6,660,907 B2
(45) Date of Patent: Dec. 9, 2003

(54) GENES ENCODING SCIP-1 ORTHOLOGS AND METHODS OF USE

(75) Inventors: Carol A. Hendrick, Des Moines, IA (US); Xu Hu, Urbandale, IA (US); Guihua Lu, Urbandale, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 102 days.

(21) Appl. No.: 09/902,331

(22) Filed: Jul. 10, 2001

(65) Prior Publication Data

US 2002/0069428 A1 Jun. 6, 2002

Related U.S. Application Data

(60) Provisional application No. 60/217,156, filed on Jul. 10, 2000.

(51) Int. Cl.[7] .................... C12N 5/09; C12N 15/29; C12N 15/82; A01H 5/00; A01H 5/10
(52) U.S. Cl. .................... 800/279; 800/278; 800/298; 800/295; 800/320; 800/320.1; 800/320.2; 800/320.3; 800/317; 800/317.1; 800/317.2; 800/312; 800/322; 800/286; 435/320.1; 435/419; 435/468; 536/23.1; 536/23.6; 536/24.1; 536/24.5
(58) Field of Search .................... 800/279, 278, 800/298, 320, 295, 320.1, 320.2, 317, 317.2, 312, 322, 320.3, 286; 435/320.1, 419, 468; 536/23.1, 24.1, 23.6, 24.5

(56) References Cited

U.S. PATENT DOCUMENTS 6,083,712 A 7/2000 Birch et al.

OTHER PUBLICATIONS

Bork et al. Genome Research, vol. 10, pp. 398–400, 2000.*
Lazar et al. Molecular and Cellular Biology, vol. 8(3), pp. 1247–1252, 1988.*
Broun et al Science, vol. 282, pp. 131–133, 1998.*
Science Journal, vol. 292, pp. 1486–1487, 2001.*
NCBI Accession No. A38246.
NCBI Accession No. C27062.
NCBI Accession No. U39938.
NCBI Accession No. X78345.
NCBI Accession No. Z17627.
NCBI Accession No. AI032451.
NCBI Accession No. AI442274.
NCBI Accession No. AAB89551.
NCBI Accession No. AAC68331.
NCBI Accession No. AAC73646.
NCBI Accession No. AAD19015.
NCBI Accession No. BAA11717.
NCBI Accession No. BAA30372.
NCBI Accession No. CAB08635.
NCBI Accession No. CAB45286.
NCBI Accession No. CAB50064.

* cited by examiner

Primary Examiner—Elizabeth F. McElwain
Assistant Examiner—Medina A. Ibrahim
(74) Attorney, Agent, or Firm—Pioneer Hi-Bred International, Inc.

(57) ABSTRACT

Compositions and methods for enhancing the resistance of plants to pests and for altering the level of biotin in plants are provided. Nucleotide sequences isolated from soybean, rice, maize, and wheat are provided. The nucleotide sequences encode orthologs of sunflower SCIP-1. Also provided are the SCIP-1 proteins encoded by such nucleotide sequences. The methods involve transforming plants with the SCIP-1 nucleotide sequences to enhance the plant's resistance to plant pests or to alter the level of biotin in the plant. Transformed plants, plant cells, tissues, and seeds are also provided.

19 Claims, No Drawings

SEQUENCE LISTING

<160> NUMBER OF SEQ ID NOS: 16

<210> SEQ ID NO 1
<211> LENGTH: 776

```
<212> TYPE: DNA
<213> ORGANISM: Glycine max
<220> FEATURE:
<221> NAME/KEY: CDS
<222> LOCATION: (43)..(552)

<400> SEQUENCE: 1
aaaaagaaag cacgttgaag attgtaactt gtaacaacaa ct atg gct agc gat         54
                                              Met Ala Ser Asp
                                                1 ggc agc gaa gag ttc agg cta gtg tca ccg gcg ttc aaa aac ggg ggg       102
Gly Ser Glu Glu Phe Arg Leu Val Ser Pro Ala Phe Lys Asn Gly Gly
  5              10                  15                  20 aag tta ccg agg cac tac acc gac gat ggt cag ggt acg aag aag aac      150
Lys Leu Pro Arg His Tyr Thr Asp Asp Gly Gln Gly Thr Lys Lys Asn
                 25                  30                  35 ata tcc cct cca ttg gag tgg tat aac ctt ccg gag ggg acg aag act      198
Ile Ser Pro Pro Leu Glu Trp Tyr Asn Leu Pro Glu Gly Thr Lys Thr
         40                  45                  50 ctt gcc ctc gtg gtg gag gat att gat gcg acc gat tct ggt ggg ccc      246
Leu Ala Leu Val Val Glu Asp Ile Asp Ala Thr Asp Ser Gly Gly Pro
 55                  60                  65 atg gtg cca tgg act cac cgg gtc gtc gca aac atc ttg gcc acg gtg      294
Met Val Pro Trp Thr His Arg Val Val Ala Asn Ile Leu Ala Thr Val
 70                  75                  80 aag ggc ttg ccg gag gga ttt tct ggc aag tcg gcc gag atg ggg ggc      342
Lys Gly Leu Pro Glu Gly Phe Ser Gly Lys Ser Ala Glu Met Gly Gly
 85                  90                  95                 100 gac tac gcg gcg atc aag gag ggg aac aat gac ctg aag gtg cca ggg      390
Asp Tyr Ala Ala Ile Lys Glu Gly Asn Asn Asp Leu Lys Val Pro Gly
                105                 110                 115 tgg aat ggg ccc agg ctg ccc acg cct gga cac agg att cag ttt agg      438
Trp Asn Gly Pro Arg Leu Pro Thr Pro Gly His Arg Ile Gln Phe Arg
            120                 125                 130 ctc tat gct ttg gat gat gag ctc aag ctt ggt aat aag ttg acg aag      486
Leu Tyr Ala Leu Asp Asp Glu Leu Lys Leu Gly Asn Lys Leu Thr Lys
        135                 140                 145 gag aag ttg ttg gaa gat acc att gaa gga cat gtg tta gga gaa gcg      534
Glu Lys Leu Leu Glu Asp Thr Ile Glu Gly His Val Leu Gly Glu Ala
150                 155                 160 acc ttg atg gct ata ttc taatgtaaca acatattgtg ggtgcattgt              582
Thr Leu Met Ala Ile Phe
165                 170 ctttggcttt atacatgtac cattttaaaa gtgttaggag aagcgacctt gatggctata    642
ttctaatgta acaacatatt gtgggtgcat tgtcttggc tttatacatg taccatttta    702
aaagtgtgtc atcaacgaga taaacatttt accaaatatc actttgactt ccgtaaaaaa    762
aaaaaaaaaa aaaa                                                      776

<210> SEQ ID NO 2
<211> LENGTH: 170
<212> TYPE: PRT
<213> ORGANISM: Glycine max

<400> SEQUENCE: 2

Met Ala Ser Asp Gly Ser Glu Glu Phe Arg Leu Val Ser Pro Ala Phe
  1               5                  10                  15

Lys Asn Gly Gly Lys Leu Pro Arg His Tyr Thr Asp Asp Gly Gln Gly
                 20                  25                  30

Thr Lys Lys Asn Ile Ser Pro Pro Leu Glu Trp Tyr Asn Leu Pro Glu
```

-continued

```
                35                  40                  45
Gly Thr Lys Thr Leu Ala Leu Val Val Glu Asp Ile Asp Ala Thr Asp
         50                  55                  60
Ser Gly Gly Pro Met Val Pro Trp Thr His Arg Val Val Ala Asn Ile
 65                  70                  75                  80
Leu Ala Thr Val Lys Gly Leu Pro Glu Gly Phe Ser Gly Lys Ser Ala
                 85                  90                  95
Glu Met Gly Gly Asp Tyr Ala Ala Ile Lys Glu Gly Asn Asn Asp Leu
            100                 105                 110
Lys Val Pro Gly Trp Asn Gly Pro Arg Leu Pro Thr Pro Gly His Arg
        115                 120                 125
Ile Gln Phe Arg Leu Tyr Ala Leu Asp Asp Glu Leu Lys Leu Gly Asn
    130                 135                 140
Lys Leu Thr Lys Glu Lys Leu Leu Glu Asp Thr Ile Glu Gly His Val
145                 150                 155                 160
Leu Gly Glu Ala Thr Leu Met Ala Ile Phe
                165                 170

<210> SEQ ID NO 3
<211> LENGTH: 776
<212> TYPE: DNA
<213> ORGANISM: Oryza sativa
<220> FEATURE:
<221> NAME/KEY: CDS
<222> LOCATION: (106)..(606)

<400> SEQUENCE: 3
cttacatgta agctcgtgcc gaattcggca cgagcttaca gccacgagcg cgaagcgaac      60
acacgaagcg ttcgtcaagc aagaacagag tttgtttgtg ccgcg atg gcg cag gag    117
                                                Met Ala Gln Glu
                                                  1 agc ctg agg ctg gtg tcg cac ccg atc gcg gcg cac gag ggg cgg ctg      165
Ser Leu Arg Leu Val Ser His Pro Ile Ala Ala His Glu Gly Arg Leu
  5                  10                  15                  20 ccg cgg cac tac acg ctg gag ggg cag ggc gcg aag aag gac atc tcg      213
Pro Arg His Tyr Thr Leu Glu Gly Gln Gly Ala Lys Lys Asp Ile Ser
                 25                  30                  35 ccg ccg gtg gag tgg tac ggg gtg ccc gac ggg acg cgg tcg ctg gcg      261
Pro Pro Val Glu Trp Tyr Gly Val Pro Asp Gly Thr Arg Ser Leu Ala
             40                  45                  50 ctg gtg gtg cac gac gtc gac gcc ccg gac ccg gac ggc ccc atc gtg      309
Leu Val Val His Asp Val Asp Ala Pro Asp Pro Asp Gly Pro Ile Val
         55                  60                  65 ccg tgg acg cac tgg gtc gtc gcc aac atc ccg ccc tcc gtc aag ggc      357
Pro Trp Thr His Trp Val Val Ala Asn Ile Pro Pro Ser Val Lys Gly
     70                  75                  80 ctc ccc gag ggc ttc tcc ggc aag gag ggc gcc gcc gcc cgc gag tac      405
Leu Pro Glu Gly Phe Ser Gly Lys Glu Gly Ala Ala Ala Arg Glu Tyr
 85                  90                  95                 100 ggc ggc atc cag gag ggc gtc aac gac tgg aag cag ccc ggc tgg cgc      453
Gly Gly Ile Gln Glu Gly Val Asn Asp Trp Lys Gln Pro Gly Trp Arg
                105                 110                 115 ggc ccc atc cct ccc tcc cgc ggc cac cgc atc cag ttc aag ctg tac      501
Gly Pro Ile Pro Pro Ser Arg Gly His Arg Ile Gln Phe Lys Leu Tyr
            120                 125                 130 gcc ctc gac gac gag gtg cac ctc ggc aac aag gtg acc aag gac aag      549
Ala Leu Asp Asp Glu Val His Leu Gly Asn Lys Val Thr Lys Asp Lys
        135                 140                 145
```

-continued

```
ctg atg gac gcc atc gag ggg cat gtg ctg gga gaa gcc gag ctc atg     597
Leu Met Asp Ala Ile Glu Gly His Val Leu Gly Glu Ala Glu Leu Met
    150                 155                 160 gcc gtc ttc taggacgcga gctctctgca ttttgacacc cctgtgagac             646
Ala Val Phe
165 tgttctttgc agagcttgta ccatatcaca aacttgttga acttttatcc aataaaaaac   706 aagtcacttg ggtggtggtg ttattgaaaa aaaaaaaaaa aaaaaaaaaa aaaaaaaaaa   766 aaaaaaaaaa                                                          776

<210> SEQ ID NO 4
<211> LENGTH: 167
<212> TYPE: PRT
<213> ORGANISM: Oryza sativa

<400> SEQUENCE: 4

Met Ala Gln Glu Ser Leu Arg Leu Val Ser His Pro Ile Ala Ala His
  1               5                  10                  15

Glu Gly Arg Leu Pro Arg His Tyr Thr Leu Glu Gly Gln Gly Ala Lys
                 20                  25                  30

Lys Asp Ile Ser Pro Pro Val Glu Trp Tyr Gly Val Pro Asp Gly Thr
             35                  40                  45

Arg Ser Leu Ala Leu Val Val His Asp Val Asp Ala Pro Asp Pro Asp
         50                  55                  60

Gly Pro Ile Val Pro Trp Thr His Trp Val Val Ala Asn Ile Pro Pro
 65                  70                  75                  80

Ser Val Lys Gly Leu Pro Glu Gly Phe Ser Gly Lys Glu Gly Ala Ala
                 85                  90                  95

Ala Arg Glu Tyr Gly Gly Ile Gln Glu Gly Val Asn Asp Trp Lys Gln
                100                 105                 110

Pro Gly Trp Arg Gly Pro Ile Pro Pro Ser Arg Gly His Arg Ile Gln
            115                 120                 125

Phe Lys Leu Tyr Ala Leu Asp Asp Glu Val His Leu Gly Asn Lys Val
        130                 135                 140

Thr Lys Asp Lys Leu Met Asp Ala Ile Glu Gly His Val Leu Gly Glu
145                 150                 155                 160

Ala Glu Leu Met Ala Val Phe
                165

<210> SEQ ID NO 5
<211> LENGTH: 758
<212> TYPE: DNA
<213> ORGANISM: Zea mays
<220> FEATURE:
<221> NAME/KEY: CDS
<222> LOCATION: (104)..(631)

<400> SEQUENCE: 5
ggcacgagcg gaactgacta gaactagtac gtagatccaa cactcgggac gaaattaaaa    60
gagacgacgc acatcaacca gcaggcatcg cgcggtcacc acc atg gcg gcg cag    115
                                              Met Ala Ala Gln
                                                1 gag ggc ggc atg agg ctg gtg tcg cac ccg atc gcg gcg cac gac ggg    163
Glu Gly Gly Met Arg Leu Val Ser His Pro Ile Ala Ala His Asp Gly
  5                  10                  15                  20 cgg ctg ccg cgg cag tac acg gcg gag ggg cag ggc gcc aag aag gac    211
Arg Leu Pro Arg Gln Tyr Thr Ala Glu Gly Gln Gly Ala Lys Lys Asp
                 25                  30                  35
```

```
atg tcg ccg ccg ctg gag tgg tac ggc gtg ccc gag ggc gcg cgg tcg      259
Met Ser Pro Pro Leu Glu Trp Tyr Gly Val Pro Glu Gly Ala Arg Ser
            40                  45                  50 ctg gcg ctg ctg gtg cag gac atc gac gcc gac ccc agc gtg ccg tgg      307
Leu Ala Leu Leu Val Gln Asp Ile Asp Ala Asp Pro Ser Val Pro Trp
        55                  60                  65 acg cac tgg gtg gtg gcc aac atc ccg ccc gcc acc agg ggc ctc ccc      355
Thr His Trp Val Val Ala Asn Ile Pro Pro Ala Thr Arg Gly Leu Pro
    70                  75                  80 gag ggg ttc tcc ggc gcc gcg ggg ccg ggg gcg ggg gcg ggc cgc gac      403
Glu Gly Phe Ser Gly Ala Ala Gly Pro Gly Ala Gly Ala Gly Arg Asp
85                  90                  95                 100 cag ctc ggc ggc ctg cag gag ggg gtc aac gac tgg aag cag ccc ggc      451
Gln Leu Gly Gly Leu Gln Glu Gly Val Asn Asp Trp Lys Gln Pro Gly
                105                 110                 115 tgg cgc ggg ccc gtg ccg ccc tcc cac ggc cac cgc atc cag ttc aag      499
Trp Arg Gly Pro Val Pro Pro Ser His Gly His Arg Ile Gln Phe Lys
            120                 125                 130 ctc tac gcg ctc gac gac gag gtg cac ctc ggc aac aag gtg acc agg      547
Leu Tyr Ala Leu Asp Asp Glu Val His Leu Gly Asn Lys Val Thr Arg
        135                 140                 145 gat aag ctc atg gag gcg atc gac ggg cac gtg ctg gaa gaa gcc gag      595
Asp Lys Leu Met Glu Ala Ile Asp Gly His Val Leu Glu Glu Ala Glu
    150                 155                 160 ctg atc gcc gtg ttc cag gga gtc gtc gcc aac aac taacacacac           641
Leu Ile Ala Val Phe Gln Gly Val Val Ala Asn Asn
165                 170                 175 tctcagagat atctttgttg gcgtgctttg tatttgcttg tgtggctacc atgtaatttt    701
gatcgaataa aagggaactt cccaaaaaaa aaaaaaaaaa aaaaaaaaaa aaaaaaa       758

<210> SEQ ID NO 6
<211> LENGTH: 176
<212> TYPE: PRT
<213> ORGANISM: Zea mays

<400> SEQUENCE: 6

Met Ala Ala Gln Glu Gly Gly Met Arg Leu Val Ser His Pro Ile Ala
1               5                   10                  15

Ala His Asp Gly Arg Leu Pro Arg Gln Tyr Thr Ala Glu Gly Gln Gly
            20                  25                  30

Ala Lys Lys Asp Met Ser Pro Pro Leu Glu Trp Tyr Gly Val Pro Glu
        35                  40                  45

Gly Ala Arg Ser Leu Ala Leu Leu Val Gln Asp Ile Asp Ala Asp Pro
    50                  55                  60

Ser Val Pro Trp Thr His Trp Val Val Ala Asn Ile Pro Pro Ala Thr
65                  70                  75                  80

Arg Gly Leu Pro Glu Gly Phe Ser Gly Ala Ala Gly Pro Gly Ala Gly
                85                  90                  95

Ala Gly Arg Asp Gln Leu Gly Gly Leu Gln Glu Gly Val Asn Asp Trp
            100                 105                 110

Lys Gln Pro Gly Trp Arg Gly Pro Val Pro Pro Ser His Gly His Arg
        115                 120                 125

Ile Gln Phe Lys Leu Tyr Ala Leu Asp Asp Glu Val His Leu Gly Asn
    130                 135                 140

Lys Val Thr Arg Asp Lys Leu Met Glu Ala Ile Asp Gly His Val Leu
145                 150                 155                 160
```

```
Glu Glu Ala Glu Leu Ile Ala Val Phe Gln Gly Val Val Ala Asn Asn
            165                 170                 175

<210> SEQ ID NO 7
<211> LENGTH: 731
<212> TYPE: DNA
<213> ORGANISM: Zea mays
<220> FEATURE:
<221> NAME/KEY: CDS
<222> LOCATION: (87)..(608)

<400> SEQUENCE: 7
ccacgcgtcc gactgactag aactagtacg tagaaatcca acactcggga cgaaattaaa        60
agagacgaga cgacgcatca tccggc atg gcg gcg cag gag ggc ggc atg agg       113
                             Met Ala Ala Gln Glu Gly Gly Met Arg
                              1               5 ctg gtg tcg cac ccg atc gcg gcg cac gac ggg cgg ctg ccg cgg cag       161
Leu Val Ser His Pro Ile Ala Ala His Asp Gly Arg Leu Pro Arg Gln
 10              15                  20                  25 tac acg gcg gag ggg cag ggc gcc aag aag gac atg tcg ccg ccg ctg       209
Tyr Thr Ala Glu Gly Gln Gly Ala Lys Lys Asp Met Ser Pro Pro Leu
                 30                  35                  40 gaa tgg tac ggc gtg ccc gag ggc gcg cgg tcg ctg gcg ctg ctg gtg       257
Glu Trp Tyr Gly Val Pro Glu Gly Ala Arg Ser Leu Ala Leu Leu Val
             45                  50                  55 cag gac atc gac gcc gac ccc atc gtg ccg tgg acg cac tgg gtg gtg       305
Gln Asp Ile Asp Ala Asp Pro Ile Val Pro Trp Thr His Trp Val Val
 60                  65                  70 gcc aac atc ccg ccc gcc acc agg ggc ctc ccc gag ggg ttc tcc ggc       353
Ala Asn Ile Pro Pro Ala Thr Arg Gly Leu Pro Glu Gly Phe Ser Gly
     75                  80                  85 gcc gcg ggg gcg ggg ccg ggc cgc gac cag ctc ggc gga ctg cag gag       401
Ala Ala Gly Ala Gly Pro Gly Arg Asp Gln Leu Gly Gly Leu Gln Glu
 90                  95                 100                 105 ggg gtc aac gac tgg aag cag ccc ggc tgg cgc ggg ccc gtg ccg ccc       449
Gly Val Asn Asp Trp Lys Gln Pro Gly Trp Arg Gly Pro Val Pro Pro
                 110                 115                 120 tcc cac ggc cac cgc atc cag ttc aag ctc tac gcg ctc gac gac gag       497
Ser His Gly His Arg Ile Gln Phe Lys Leu Tyr Ala Leu Asp Asp Glu
             125                 130                 135 gtg cac ctc ggc aac aag gtg acc agg gat aag ctc atg gag gcg atc       545
Val His Leu Gly Asn Lys Val Thr Arg Asp Lys Leu Met Glu Ala Ile
         140                 145                 150 gac ggg cac gtg ctg gaa gaa gcc gag ctg atc gcc gtg ttc cag gga       593
Asp Gly His Val Leu Glu Glu Ala Glu Leu Ile Ala Val Phe Gln Gly
 155                 160                 165 gtc gtc gcc aac aac taacacacac actcagagat atctttgttg gcgtgctttg       648
Val Val Ala Asn Asn
170 tatttgcttg tgtggctacc atgtaatttt gatcgaataa aagggaactt cacatgtgct       708 taaaaaaaaa aaaaaaaaaa aaa                                                731

<210> SEQ ID NO 8
<211> LENGTH: 174
<212> TYPE: PRT
<213> ORGANISM: Zea mays

<400> SEQUENCE: 8

Met Ala Ala Gln Glu Gly Gly Met Arg Leu Val Ser His Pro Ile Ala
 1               5                  10                  15
```

```
Ala His Asp Gly Arg Leu Pro Arg Gln Tyr Thr Ala Glu Gly Gln Gly
         20                  25                  30

Ala Lys Lys Asp Met Ser Pro Pro Leu Glu Trp Tyr Gly Val Pro Glu
         35                  40                  45

Gly Ala Arg Ser Leu Ala Leu Leu Val Gln Asp Ile Asp Ala Asp Pro
     50                  55                  60

Ile Val Pro Trp Thr His Trp Val Val Ala Asn Ile Pro Pro Ala Thr
 65                  70                  75                  80

Arg Gly Leu Pro Glu Gly Phe Ser Gly Ala Ala Gly Ala Gly Pro Gly
                 85                  90                  95

Arg Asp Gln Leu Gly Gly Leu Gln Glu Gly Val Asn Asp Trp Lys Gln
            100                 105                 110

Pro Gly Trp Arg Gly Pro Val Pro Ser His Gly His Arg Ile Gln
        115                 120                 125

Phe Lys Leu Tyr Ala Leu Asp Asp Glu Val His Leu Gly Asn Lys Val
    130                 135                 140

Thr Arg Asp Lys Leu Met Glu Ala Ile Asp Gly His Val Leu Glu Glu
145                 150                 155                 160

Ala Glu Leu Ile Ala Val Phe Gln Gly Val Val Ala Asn Asn
                165                 170

<210> SEQ ID NO 9
<211> LENGTH: 760
<212> TYPE: DNA
<213> ORGANISM: Triticum aestivum
<220> FEATURE:
<221> NAME/KEY: CDS
<222> LOCATION: (106)..(621)

<400> SEQUENCE: 9
ggaattcggc acgagctgac tagaactagt acgtagatcc aacactcggg acgaaattaa      60
aagagacgac gcacatcaac cagcaggcat cgcgcggtca ccacc atg gcg gcg cag     117
                                               Met Ala Ala Gln
                                                 1 gag ggc ggc atg agg ctg gtg tcg cac ccg atc gcg gcg cac gac ggg       165
Glu Gly Gly Met Arg Leu Val Ser His Pro Ile Ala Ala His Asp Gly
  5                  10                  15                  20 cgg ctg ccg cgg cag tac acg gcg gag ggg cag ggc gcc aag aag gac       213
Arg Leu Pro Arg Gln Tyr Thr Ala Glu Gly Gln Gly Ala Lys Lys Asp
                 25                  30                  35 atg tcg ccg ccg ctg gag tgg tac ggc gtg ccc gag ggc gcg cgg tcg       261
Met Ser Pro Pro Leu Glu Trp Tyr Gly Val Pro Glu Gly Ala Arg Ser
         40                  45                  50 ctg gcg ctg ctg gtg cag gac atc gac gcc gac ccc agc gtg ccg tgg       309
Leu Ala Leu Leu Val Gln Asp Ile Asp Ala Asp Pro Ser Val Pro Trp
     55                  60                  65 acg cac tgg gtg gtg gcc aac atc ccg ccc gcc acc agg ggc ctc ccc       357
Thr His Trp Val Val Ala Asn Ile Pro Pro Ala Thr Arg Gly Leu Pro
 70                  75                  80 gag ggg ttc tcc ggc gcc gcg ggg gcg ggc cgc gac cag ctc ggc ggc       405
Glu Gly Phe Ser Gly Ala Ala Gly Ala Gly Arg Asp Gln Leu Gly Gly
             85                  90                  95                 100 ctg cag gag ggg gtc aac gac tgg aag cag ccc ggc tgg cgc ggg ccc       453
Leu Gln Glu Gly Val Asn Asp Trp Lys Gln Pro Gly Trp Arg Gly Pro
                105                 110                 115 gtg ccg ccc tcc cac ggc cac cgc atc cag ttc aag ctc tac gcg ctc       501
Val Pro Pro Ser His Gly His Arg Ile Gln Phe Lys Leu Tyr Ala Leu
            120                 125                 130
```

```
gac gac gag gtg cac ctc ggc aac aag gtg acc agg gat aag ctc atg      549
Asp Asp Glu Val His Leu Gly Asn Lys Val Thr Arg Asp Lys Leu Met
        135                 140                 145 gag gcg atc gac ggg cac gtg ctg gaa gaa gcc gag ctg atc gcc gtg      597
Glu Ala Ile Asp Gly His Val Leu Glu Glu Ala Glu Leu Ile Ala Val
    150                 155                 160 ttc cag gga gtc gtc gcc aac aac taacacacac actcagagat atctttgttt     651
Phe Gln Gly Val Val Ala Asn Asn
165                 170 gcgtgctttg tatttgcttg tgtggctacc atgtaatttt gatcgaataa aagggaactt    711
cccaaaaaaa aaaaaaaaaa aaaaaaaaaa aaaaaaaaaa aaaaaaaaa                760

<210> SEQ ID NO 10
<211> LENGTH: 172
<212> TYPE: PRT
<213> ORGANISM: Triticum aestivum

<400> SEQUENCE: 10

Met Ala Ala Gln Glu Gly Gly Met Arg Leu Val Ser His Pro Ile Ala
 1               5                  10                  15

Ala His Asp Gly Arg Leu Pro Arg Gln Tyr Thr Ala Glu Gly Gln Gly
            20                  25                  30

Ala Lys Lys Asp Met Ser Pro Leu Glu Trp Tyr Gly Val Pro Glu
        35                  40                  45

Gly Ala Arg Ser Leu Ala Leu Leu Val Gln Asp Ile Asp Ala Asp Pro
    50                  55                  60

Ser Val Pro Trp Thr His Trp Val Val Ala Asn Ile Pro Pro Ala Thr
65                  70                  75                  80

Arg Gly Leu Pro Glu Gly Phe Ser Gly Ala Ala Gly Ala Gly Arg Asp
                85                  90                  95

Gln Leu Gly Gly Leu Gln Glu Gly Val Asn Asp Trp Lys Gln Pro Gly
            100                 105                 110

Trp Arg Gly Pro Val Pro Pro Ser His Gly His Arg Ile Gln Phe Lys
        115                 120                 125

Leu Tyr Ala Leu Asp Asp Glu Val His Leu Gly Asn Lys Val Thr Arg
    130                 135                 140

Asp Lys Leu Met Glu Ala Ile Asp Gly His Val Leu Glu Glu Ala Glu
145                 150                 155                 160

Leu Ile Ala Val Phe Gln Gly Val Val Ala Asn Asn
                165                 170

<210> SEQ ID NO 11
<211> LENGTH: 685
<212> TYPE: DNA
<213> ORGANISM: Triticum aestivum
<220> FEATURE:
<221> NAME/KEY: CDS
<222> LOCATION: (28)..(522)

<400> SEQUENCE: 11
cagaggggcc ggccggcgag aagcgag atg gcg cag gag agc ctg agg ctg gtg    54
                            Met Ala Gln Glu Ser Leu Arg Leu Val
                             1               5 tgc ccg ccg gtg tcg gcg cac gag ggg cgg ctg ccg cgg cag tac acg     102
Cys Pro Pro Val Ser Ala His Glu Gly Arg Leu Pro Arg Gln Tyr Thr
 10                  15                  20                  25 ctg gag ggg cag ggc gcg aag aag gac atc tcg ccg ccg ctg gag tgg    150
Leu Glu Gly Gln Gly Ala Lys Lys Asp Ile Ser Pro Pro Leu Glu Trp
                30                  35                  40
```

```
tac ggg gtg ccc gac ggc acg cgg tcg ctg gcg gtg gtg gtg cag gac      198
Tyr Gly Val Pro Asp Gly Thr Arg Ser Leu Ala Val Val Val Gln Asp
                 45                  50                  55 gtg gac gcg gac gag cgg gtg ccc tgg acg cac tgg gtg gtc gtc aac      246
Val Asp Ala Asp Glu Arg Val Pro Trp Thr His Trp Val Val Val Asn
             60                  65                  70 atc tcg ccc gag gag aag ggc ctg ccc gag ggc ttc tcc ggc gcc ggg      294
Ile Ser Pro Glu Glu Lys Gly Leu Pro Glu Gly Phe Ser Gly Ala Gly
 75                  80                  85 ggc aac gcc aac gcc ggg ggc gac ggc ggc gtc cag gag ggg gtc          342
Gly Asn Ala Asn Ala Gly Gly Asp Gly Gly Val Gln Glu Gly Val
 90                  95                 100                 105 aac gac tgg aag cag ccc ggg tgg cgc ggc ccc gtc ccc gac tcc cac      390
Asn Asp Trp Lys Gln Pro Gly Trp Arg Gly Pro Val Pro Asp Ser His
             110                 115                 120 ggc cac cgc atc cag ttc cgt ctc tac gcg ctc gac gac ctg ctc agc      438
Gly His Arg Ile Gln Phe Arg Leu Tyr Ala Leu Asp Asp Leu Leu Ser
                 125                 130                 135 ctc ggc aac aag gtg aca gtg gac aag gtc atg gag gcc atc gag ggg      486
Leu Gly Asn Lys Val Thr Val Asp Lys Val Met Glu Ala Ile Glu Gly
             140                 145                 150 cac gtg ctg ggg gag gcc gag atc acg gct gtg ttc taaggagctc           532
His Val Leu Gly Glu Ala Glu Ile Thr Ala Val Phe
 155                 160                 165 tgtggatttt ggcactcggc tctgtgtgtc tgaccttgtt acttctcctt gccaatcgtg    592
tgtggtctgt tctgtagcgt gcttgtatac gcatggcaac gaccagcctt tgtaattttg    652
aaccaataag tgaagtaacc ttttaaaaaa ggg                                 685

<210> SEQ ID NO 12
<211> LENGTH: 165
<212> TYPE: PRT
<213> ORGANISM: Triticum aestivum

<400> SEQUENCE: 12

Met Ala Gln Glu Ser Leu Arg Leu Val Cys Pro Pro Val Ser Ala His
 1               5                  10                  15

Glu Gly Arg Leu Pro Arg Gln Tyr Thr Leu Glu Gly Gln Gly Ala Lys
             20                  25                  30

Lys Asp Ile Ser Pro Pro Leu Glu Trp Tyr Gly Val Pro Asp Gly Thr
         35                  40                  45

Arg Ser Leu Ala Val Val Gln Asp Val Asp Ala Asp Glu Arg Val
     50                  55                  60

Pro Trp Thr His Trp Val Val Asn Ile Ser Pro Glu Glu Lys Gly
 65                  70                  75                  80

Leu Pro Glu Gly Phe Ser Gly Ala Gly Gly Asn Ala Asn Ala Gly Gly
                 85                  90                  95

Gly Asp Gly Gly Val Gln Glu Gly Val Asn Asp Trp Lys Gln Pro Gly
             100                 105                 110

Trp Arg Gly Pro Val Pro Asp Ser His Gly His Arg Ile Gln Phe Arg
         115                 120                 125

Leu Tyr Ala Leu Asp Asp Leu Leu Ser Leu Gly Asn Lys Val Thr Val
     130                 135                 140

Asp Lys Val Met Glu Ala Ile Glu Gly His Val Leu Gly Glu Ala Glu
145                 150                 155                 160

Ile Thr Ala Val Phe
                165
```

<210> SEQ ID NO 13
<211> LENGTH: 759
<212> TYPE: DNA
<213> ORGANISM: Triticum aestivum
<220> FEATURE:
<221> NAME/KEY: CDS
<222> LOCATION: (69)..(563)

<400> SEQUENCE: 13

```
acaatccagc aaactcatcg cacgaggatc aacagcagca gagagaagca aaccggccgg      60 ccggcgag atg gcg cag gag agc ctg agg ctg gtg tgc ccg ccg gtg tcg     110
         Met Ala Gln Glu Ser Leu Arg Leu Val Cys Pro Pro Val Ser
         1               5                  10 gcg cac gag ggg cgg ctg ccg cgg cag tac acg ctg gag ggg cag ggc      158
Ala His Glu Gly Arg Leu Pro Arg Gln Tyr Thr Leu Glu Gly Gln Gly
 15                  20                  25                  30 gcg aag aag gac atc tcg ccg ccg ctg gag tgg tac ggg gtg ccc gac      206
Ala Lys Lys Asp Ile Ser Pro Pro Leu Glu Trp Tyr Gly Val Pro Asp
                 35                  40                  45 ggc acg cgg tcg ctg gcg gtg gtg gtg cag gac gtc gac gcg gac gag      254
Gly Thr Arg Ser Leu Ala Val Val Val Gln Asp Val Asp Ala Asp Glu
             50                  55                  60 cgg gtg ccg tgg acg cac tgg gtg gtc gtc aac atc tcg ccc gag gag      302
Arg Val Pro Trp Thr His Trp Val Val Val Asn Ile Ser Pro Glu Glu
 65                  70                  75 aag ggc ctg ccc gag ggc ttc tcc ggc gcc ggg ggc aac gcc aac gcc      350
Lys Gly Leu Pro Glu Gly Phe Ser Gly Ala Gly Gly Asn Ala Asn Ala
 80                  85                  90 ggc ggc ggc gac ggc ggc gtc cag gag ggg gtc aac gac tgg aag cag      398
Gly Gly Gly Asp Gly Gly Val Gln Glu Gly Val Asn Asp Trp Lys Gln
 95                 100                 105                 110 ccc ggg tgg cgc ggc ccc gtc ccg gac tcc cac ggc cac cgc atc cag      446
Pro Gly Trp Arg Gly Pro Val Pro Asp Ser His Gly His Arg Ile Gln
                115                 120                 125 ttc cgg cta tac gcg ctc gac gac gtg ctc agc ctc ggc aac aag gtg      494
Phe Arg Leu Tyr Ala Leu Asp Asp Val Leu Ser Leu Gly Asn Lys Val
            130                 135                 140 act gtg gac aag gtc atg gag gcc atc gag ggg cac gtg ctg ggg gag      542
Thr Val Asp Lys Val Met Glu Ala Ile Glu Gly His Val Leu Gly Glu
145                 150                 155 gcc gag atc acg gcc gtg ttc taaggagttc ttgtggattt tgacactcgg         593
Ala Glu Ile Thr Ala Val Phe
        160                 165 ctctgtgtgt gtgtgtgacc tgcttgttac ttcttgcgaa ttgtgtgtgg tctgttctgt    653
agcgtgcctg tatacgcatg gccacgagca gcctttgtaa ttttgatcca ataaatgaag    713
tgacttctta tcagccgggt aacggttggg ggggccccgt acccaa                   759
```

<210> SEQ ID NO 14
<211> LENGTH: 165
<212> TYPE: PRT
<213> ORGANISM: Triticum aestivum

<400> SEQUENCE: 14

```
Met Ala Gln Glu Ser Leu Arg Leu Val Cys Pro Pro Val Ser Ala His
 1               5                  10                  15

Glu Gly Arg Leu Pro Arg Gln Tyr Thr Leu Glu Gly Gln Gly Ala Lys
             20                  25                  30

Lys Asp Ile Ser Pro Pro Leu Glu Trp Tyr Gly Val Pro Asp Gly Thr
```

```
                35                    40                    45
Arg Ser Leu Ala Val Val Gln Asp Val Asp Ala Asp Glu Arg Val
        50                    55                    60
Pro Trp Thr His Trp Val Val Asn Ile Ser Pro Glu Glu Lys Gly
 65                    70                    75                    80
Leu Pro Glu Gly Phe Ser Gly Ala Gly Gly Asn Ala Asn Ala Gly Gly
                    85                    90                    95
Gly Asp Gly Gly Val Gln Glu Gly Val Asn Asp Trp Lys Gln Pro Gly
                100                   105                   110
Trp Arg Gly Pro Val Pro Asp Ser His Gly His Arg Ile Gln Phe Arg
            115                   120                   125
Leu Tyr Ala Leu Asp Asp Val Leu Ser Leu Gly Asn Lys Val Thr Val
        130                   135                   140
Asp Lys Val Met Glu Ala Ile Glu Gly His Val Leu Gly Glu Ala Glu
145                   150                   155                   160
Ile Thr Ala Val Phe
                165

<210> SEQ ID NO 15
<211> LENGTH: 746
<212> TYPE: DNA
<213> ORGANISM: Helianthus annuus
<220> FEATURE:
<221> NAME/KEY: CDS
<222> LOCATION: (14)..(517)

<400> SEQUENCE: 15
ttcggcacga gca atg gcg aac gca agc gat gag ttc aga cta gcg tct        49
            Met Ala Asn Ala Ser Asp Glu Phe Arg Leu Ala Ser
             1               5                  10 tcc ggc atc gat cat gaa ggc cga cta cca cga aaa tac acc ggt gac       97
Ser Gly Ile Asp His Glu Gly Arg Leu Pro Arg Lys Tyr Thr Gly Asp
         15                  20                  25 ggt caa ggt aca aaa aaa gac ata tca cca ccg tta gaa tgg tac aac      145
Gly Gln Gly Thr Lys Lys Asp Ile Ser Pro Pro Leu Glu Trp Tyr Asn
 30                  35                  40 gtt ccg gag ggg aca aaa aca cta gca cta gtg gtg gag gac atc gat      193
Val Pro Glu Gly Thr Lys Thr Leu Ala Leu Val Val Glu Asp Ile Asp
 45                  50                  55                  60 gca ccg gac cca gaa gcg ccg ctg gtt ccg tgg act gtg tgg gtg gtg      241
Ala Pro Asp Pro Glu Ala Pro Leu Val Pro Trp Thr Val Trp Val Val
                 65                  70                  75 gtc aat ata cca cct act ttg aag ggg ctc cca gag gga ttt tcc ggg      289
Val Asn Ile Pro Pro Thr Leu Lys Gly Leu Pro Glu Gly Phe Ser Gly
             80                  85                  90 aaa gag ggg gac atg ggt ggc gat tat gct aat gtt aaa gaa gga cat      337
Lys Glu Gly Asp Met Gly Gly Asp Tyr Ala Asn Val Lys Glu Gly His
         95                 100                 105 aat gac ttt aag gtg cct gga tgg cgc gca ccg aag atg ccc tca tcc      385
Asn Asp Phe Lys Val Pro Gly Trp Arg Ala Pro Lys Met Pro Ser Ser
    110                 115                 120 gga cac cgg ttc gag ttt aag ctg tat gcg ttg gat gaa caa gtt gag      433
Gly His Arg Phe Glu Phe Lys Leu Tyr Ala Leu Asp Glu Gln Val Glu
125                 130                 135                 140 ttg ggg aat aag gtg act aag gag aag ttg ctg gag gcg att gat ggc      481
Leu Gly Asn Lys Val Thr Lys Glu Lys Leu Leu Glu Ala Ile Asp Gly
                145                 150                 155 cat gtg gtt ggg gag gct gtt ctg atg gcc gta aat taaattgaga            527
His Val Val Gly Glu Ala Val Leu Met Ala Val Asn
```

```
                   160                 165
atggtttata tatatgttag ttgtgtgact tgtgtcatgt gtgatgttct tgttttaacg     587
tattttgaaa cagaagtgac gagagagaga gagtgtttgt tgtgtgtttt tcttgagaga     647
tcgtgaatta attatgctgt tttgcttcaa ggaatcaagc tttataaagt aaaatacaaa     707
tgtaatgctt caaccgagct aaaaaaaaaa aaaaaaaa                             746
```

<210> SEQ ID NO 16
<211> LENGTH: 168
<212> TYPE: PRT
<213> ORGANISM: Helianthus annuus

<400> SEQUENCE: 16

```
Met Ala Asn Ala Ser Asp Glu Phe Arg Leu Ala Ser Ser Gly Ile Asp
 1               5                  10                  15

His Glu Gly Arg Leu Pro Arg Lys Tyr Thr Gly Asp Gly Gln Gly Thr
             20                  25                  30

Lys Lys Asp Ile Ser Pro Pro Leu Glu Trp Tyr Asn Val Pro Glu Gly
         35                  40                  45

Thr Lys Thr Leu Ala Leu Val Val Glu Asp Ile Asp Ala Pro Asp Pro
     50                  55                  60

Glu Ala Pro Leu Val Pro Trp Thr Val Trp Val Val Asn Ile Pro
 65                  70                  75                  80

Pro Thr Leu Lys Gly Leu Pro Glu Gly Phe Ser Gly Lys Glu Gly Asp
                 85                  90                  95

Met Gly Gly Asp Tyr Ala Asn Val Lys Glu Gly His Asn Asp Phe Lys
            100                 105                 110

Val Pro Gly Trp Arg Ala Pro Lys Met Pro Ser Ser Gly His Arg Phe
        115                 120                 125

Glu Phe Lys Leu Tyr Ala Leu Asp Glu Gln Val Glu Leu Gly Asn Lys
    130                 135                 140

Val Thr Lys Glu Lys Leu Leu Glu Ala Ile Asp Gly His Val Val Gly
145                 150                 155                 160

Glu Ala Val Leu Met Ala Val Asn
                165
```

GENES ENCODING SCIP-1 ORTHOLOGS AND METHODS OF USE

CROSS-REFERENCE TO RELATED APPLICATIONS

This application claims the benefit of U.S. Provisional Application No. 60/217,156, filed Jul. 10, 2000; which is hereby incorporated herein in its entirety by reference.

FIELD OF THE INVENTION

The invention relates to the genetic manipulation of plants, particularly to transforming plants with genes that enhance disease resistance.

BACKGROUND OF THE INVENTION

Throughout their lives, plants are routinely subjected to a variety of stresses, which act to impede or alter growth and development processes. Stresses to plants may be caused by both biotic and abiotic agents. For example, biotic causes of stress include infection with a pathogen, insect feeding, and parasitism by another plant such as mistletoe, and even grazing by ruminant animals. Abiotic stresses include osmotic stress, excessive light intensity or insufficient light intensity, cold temperatures, warm temperatures, synthetic chemicals such as those used in agriculture, and excessive wind.

Because a stress negatively impacts plant growth and development processes, stress to agricultural plants has a negative economic impact expressed in the form of reduced yields, increased expenditures for pesticides or both. Developing crop plants that are better able to tolerate or even avoid stresses is desirable and will most certainly improve agricultural productivity. Given the world's both increasing human population and diminishing land area available for agriculture, improving agricultural productivity is a paramount challenge. A thorough understanding of the mechanisms used by plants to avoid or tolerate stresses may help in the development of new strategies for improving the stress tolerance of agricultural plants.

In spite of the great frequency of stresses, plants survive, and often flourish. Plants are able to do this because of the evolution of a variety of internal and external mechanisms for avoiding or tolerating stress. For example, higher plants possess leaves with waxy, water-impermeable surfaces and pores known as stomata, which serve to allow the escape of water vapor during the process of transpiration. The periphery of the stomatal pores is lined with a pair of cells known as guard cells, which control the aperture of the pore. By modifying their size and shape through a turgor-pressure-mediated process, the guard cells can completely block the pore when conditions are unfavorable for transpiration during, for example, periods of low soil-water availability. Such a stress-avoidance system allows a plant to survive conditions of water stress by reducing transpiration to nearly zero and preventing dehydration.

Plants also possess defense systems which prevent or help limit the stresses resulting from attacks by pathogens and insects. One well-known defense system against plant pathogens is known as systemic acquired resistance. Another defense system is the systemic induction of proteinase inhibitors following insect damage, which is usually referred to as the systemic wound response. In both of these defense systems, the initial impact of the pathogen or insect is transmitted via a signal or signals to other parts of the plant which results in increased expression of genes encoding proteins that are directly or indirectly inhibitory to invading organisms. The associated, systemic increase in defense gene products is known to increase the resistance of the plant to both current and future stresses from pathogens and insects.

While certain components of the systems of plants use to respond to abiotic and biotic stresses are known, most components have yet to be elucidated. Uncovering the genetic components of such systems will provide plant breeders with new targets for crop improvement strategies.

SUMMARY OF THE INVENTION

Compositions and methods for enhancing the resistance of plants to plant pests are provided. The compositions and methods find use in controlling plant pests, including fungal pathogens, viruses, nematodes, insects, and the like. Novel nucleotide sequences from soybean, rice, maize, and wheat which encode orthologs to sunflower SCIP-1 are provided. Also provided are the proteins encoded by the nucleotide sequences of the invention. The methods for enhancing resistance of plants to plant pests involve transforming a plant with nucleotide construct comprising an SCIP-1 nucleotide sequence of the invention. The nucleotide construct may additionally involve an operably linked promoter that drives expression in a plant cell. It is recognized that a variety of promoters will be useful in the invention, the choice of which will depend in part upon the desired level of expression of the SCIP-1 sequence in the plant or alternatively, in the plant organ.

Methods for altering the level of biotin in a plant are provided. The methods find use in increasing or decreasing the level of biotin in plant or part thereof. The methods involve transforming a plant with nucleotide construct comprising an SCIP-1 nucleotide sequence of the invention. In addition, the nucleotide construct may comprise an operably linked promoter that drives expression in plant cell.

Transformed plants, plant tissues, plant tissues, and seeds, as well as methods for making such plants and seeds are additionally provided.

DETAILED DESCRIPTION OF THE INVENTION

The invention is drawn to compositions comprising nucleotide sequences encoding orthologs of a novel sunflower protein, designated Sclerotinia Inducible Protein-1, or SCIP-1 (SEQ ID NO: 16), and the proteins encoded by such nucleotide sequences. See the copending application entitled "Sunflower RhoGAP, LOX, ADH, and SCIP-1 Polynucleotides and Methods of Use," U.S. Application Ser. No. 60/166,128, filed Nov. 18, 1999; herein incorporated by reference. Sunflower SCIP-1 has limited homology with hypothetical proteins from several bacteria.

Transcript levels of sunflower SCIP-1 increase in both lesion mimic transgenic plants and Sclerotinia-infected plants. The accumulation of SCIP-1 in lesion mimic and infected sunflower plants indicates that the protein may be involved in the plant defense response to Sclerotinia and other pathogens.

In particular, the present invention provides isolated nucleotide sequences encoding SCIP-1 orthologs from soybean (SEQ ID NO: 1), rice (SEQ ID NO: 3), maize (SEQ ID NOs: 5 and 7), and wheat (SEQ ID NOs: 9, 11, and 13). Also provided are isolated proteins that are encoded by the nucleotide sequences of the invention (SEQ ID NOs: 2, 4, 6, 8, 10, 12, and 14). Such nucleotide sequences find use in methods for enhancing the resistance of plants to pests, particularly pathogens, including, but not limited to, fungal pathogens, viruses, bacteria, nematodes, and the like.

Methods are provided for enhancing the resistance of plants to pests. The methods find use in agriculture particularly in the development of new cultivars of crop plants with improved resistance to plant pests. Such new cultivars are desired by both producers and consumers alike because the new cultivars can enable producers to reduce the amount of synthetic chemical pesticides that are released into the environment. The methods of the invention involve transforming a plant with a nucleotide construct comprising at least one of the nucleotide sequences of the invention operably linked to a promoter that drives expression in a plant. Promoters of interest include, but are not limited to, constitutive, tissue-preferred, wound-inducible, insect-inducible, and pathogen-inducible. Of particular interest are pathogen-inducible promoters that increase gene expression in the vicinity of an infection site within the first few hours after commencement of the infection process.

Comparison of the SCIP-1 amino acid sequences of the invention to public sequence databases revealed significant homology to an *E. coli* protein that is involved in biotin synthesis. See, PCT patent publication WO 94/08023; herein incorporated by reference. Thus, plant SCIP-1 proteins may also be involved in biotin synthesis. The methods for enhancing the resistance of a plant to pests, however, do not depend on a particular biological mechanism, only that transforming a plant with a nucleotide sequence of the invention can enhance the resistance of the plant to at least one plant pest.

Methods are provided for altering the level of biotin in a plant. The methods find use in increasing or decreasing the level of biotin in a plant, or part thereof. Biotin is a water-soluble B vitamin that serves as a coenzyme. In living organisms, biotin is usually bound to the $\epsilon$-amino group of lysine residues of certain enzymes that are involved in the transfer of carboxyl groups such as, for example, transcarboxylases and ATP-dependent biotin carboxylases. While biotin deficiency is rare in humans, there is some evidence that increasing biotin in the diet of humans and other animals may be beneficial. In animals, biotin acts as a coenzyme during the metabolism of protein, fats, and carbohydrates. In humans, increasing the level of biotin in the diet may lower blood sugar levels in type II diabetics. Additionally, increased intake of biotin may help to strengthen hair and nails. Thus, increasing the level of biotin in a plant may increase the nutritional value of the plant when consumed by humans and other animals.

The methods for altering the level of biotin in a plant involve transforming a plant with a nucleotide construct comprising an SCIP-1 nucleotide sequence of the invention. The nucleotide construct may additionally involve an operably linked promoter that drives expression in a plant. Decreasing the level of biotin can be achieved by methods such as, for example, antisense suppression, co-suppression, and chimeraplasty. Such methods are known in the art. In antisense suppression methods, an SCIP-1 nucleotide sequence can be operably linked to a promoter that drives expression in a plant for the production of antisense transcripts. In co-suppression methods, an SCIP-1 nucleotide sequence can be operably linked to a promoter that drives expression in a plant for the production of sense transcripts. With chimeraplasty, no promoter is necessary; only an SCIP-1 nucleotide sequence of the invention, or portion thereof, is used. Generally, the desired transformed plants, with either increased or decreased levels of biotin, can be determined by measuring the level of biotin in the plant, or part thereof, by conventional methods known in the art such as, for example, HPLC, GC, GC-MS, or biotin-binding methods involving avidin or streptavidin.

Compositions of the invention include nucleotide sequences and proteins that are involved in plant responses to disease and other stresses. In particular, the present invention provides for isolated nucleic acid molecules comprising nucleotide sequences encoding the amino acid sequences shown in SEQ ID NOs: 2, 4, 6, 8, 10, 12, and 14 or the nucleotide sequences encoding the DNA sequences deposited in a bacterial host as Patent Deposit Nos. PTA-1506, PTA-1508, PTA-1507, PTA-1503, and PTA-2105. Further provided are polypeptides having an amino acid sequence encoded by a nucleic acid molecule described herein, for example those set forth in SEQ ID NOs: 1, 3, 5, 7, 9, 11, and 13, those deposited in a bacterial host as Patent Deposit Nos. PTA-1506, PTA-1508, PTA-1507, PTA-1503 and PTA-2105, and fragments and variants thereof.

Plasmids containing the nucleotide sequences of the invention, particularly SEQ ID NOs. 1, 3, 5, and 7, were deposited with the Patent Depository of the American Type Culture Collection (ATCC), 10801 University Blvd., Manassas, Va., on Mar. 17, 2000 and assigned Patent Deposit Nos. PTA-1506, PTA-1508, PTA-1507, and PTA-1503, respectively. Plasmids containing the nucleotide sequences of the invention, particularly SEQ ID NOs. 9, 11, and 13, were deposited with the Patent Depository of the ATCC on Jun. 20, 2000 and assigned Patent Deposit No. PTA-2105. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

The proteins or polypeptides of the invention have SCIP-1 biological activity. By "SCIP-1 biological activity" is intended that a protein, or fragment or variant thereof, has at least one of the biological activities of a native SCIP-1 protein of the invention including, but not limited to, the ability to increase or enhance the disease resistance of a plant and the biosynthesis or accumulation of biotin in a plant.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein. Alternatively, fragments of a nucleotide sequence that are useful as hybridization probes generally do not encode fragment proteins retain biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a SCIP-1 nucleotide sequence that encodes a biologically active portion of a SCIP-1 protein of the invention will encode at least 15, 25, 30, 50, 100, or 150 contiguous amino acids, or up to the total number of amino acids present in a full-length SCIP-1 protein of the invention (for example, 170, 167, 176, and 174 amino acids for SEQ ID NOs: 2, 4, 6, and 8, respectively). Fragments of a SCIP-1 nucleotide sequence that are useful as hybridization probes or PCR primers generally need not encode a biologically active portion of a SCIP-1 protein.

Thus, a fragment of an SCIP-1 nucleotide sequence may encode a biologically active portion of a SCIP-1 protein, or it may be a fragment that can be used as a hybridization probe or PCR primer using methods disclosed below. A biologically active portion of a SCIP-1 protein can be prepared by isolating a portion of one of the SCIP-1 nucleotide sequences of the invention, expressing the encoded portion of the SCIP-1 protein (e.g., by recombinant expression in vitro), and assessing the activity of the encoded portion of the SCIP-1 protein. Nucleic acid molecules that are fragments of a SCIP-1 nucleotide sequence comprise at least 16, 20, 50, 75, 100, 150, 200, 250, 300, 350, 400, 450, 500, 550, 600, 650, 700, or 725 nucleotides, or up to the number of nucleotides present in a full-length SCIP-1 nucleotide sequence disclosed herein (for example, 776, 776, 758 ad 731 nucleotides for SEQ ID NOs: 1, 3, 5 and 7, respectively).

By "variants" is intended substantially similar sequences. For nucleotide sequences, conservative variants include those sequences that, because of the degeneracy of the genetic code, encode the amino acid sequence of one of the SCIP-1 polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a SCIP-1 protein of the invention. Generally, variants of a particular nucleotide sequence of the invention will have at least about 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein. Such variants may result from, for example, genetic polymorphism or from human manipulation. Biologically active variants of a native SCIP-1 protein of the invention will have at least about 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the SCIP-1 proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired biological activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays.

Variant nucleotide sequences and proteins also encompass sequences and proteins derived from a mutagenic and recombinogenic procedure such as DNA shuffling. With such a procedure, one or more different SCIP-1 coding sequences can be manipulated to create a new SCIP-1 possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the SCIP-1 gene of the invention and other known SCIP-1 genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire SCIP-1 sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the SCIP-1 sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire SCIP-1 sequence disclosed herein, or one or more portions thereof, may be used as a probe capable of specifically hybridizing to corresponding SCIP-1 sequences and messenger RNAs. To achieve specific hybridization under a variety of conditions, such probes include sequences that are unique among SCIP-1 sequences and are preferably at least about 10 nucleotides in length, and most preferably at least about 20 nucleotides in length. Such probes may be used to amplify corresponding SCIP-1 sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20× SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1× SSC at 55 to 60° C. Exemplary high stringency conditions include hybridization in 50% formamide, 1 M NaCl, 1% SDS at 37° C., and a wash in 0.1× SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA—DNA hybrids, the $T_m$ can be approximated from the equation of Meinkoth and Wahl (1984) *Anal. Biochem.* 138:267–284: $T_m$=81.5° C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), one method is to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for a SCIP-1 protein and which hybridize under stringent conditions to the SCIP-1 sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); thei ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731, 181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774–8778; herein incorporated by reference.

The SCIP-1 sequences of the invention are provided in expression cassettes for expression in the plant of interest. The cassette will include 5' and 3' regulatory sequences operably linked to a SCIP-1 sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the SCIP-1 sequence to be under the transcriptional regulation of the regulatory regions. The expression cassette may additionally contain selectable marker genes.

The expression cassette will include in the 5'-3' direction of transcription, a transcriptional and translational initiation region, a SCIP-1 nucleotide sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of SCIP-1 in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126–6130); potyvirus leaders, for example, TEV leader (Tobacco Etch Virus) (Gallie et al. (1995) *Gene* 165(2):233–238), MDMV leader (Maize Dwarf Mosaic Virus) (*Virology* 154:9–20), and human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, New York), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention.

A number of promoters can be used in the practice of the invention. The promoters can be selected based on the desired outcome. The nucleic acids can be combined with constitutive, tissue-preferred, or other promoters for expression in plants.

Such constitutive promoters include, for example, the core promoter of the Rsyn7 promoter and other constitutive promoters disclosed in WO 99/43838; the scp1 promoter (copending U.S. application Ser. No. 09/028,819 and WO 99/43838); the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al, (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also the copending application entitled "Inducible Maize Promoters," U.S. application Ser. No. 09/257,583, filed Feb. 25, 1999, herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225:1570–1573); WIP1 (Rohmeier et al. (1993) *Plant Mol. Biol.* 22:783–792; Eckelkamp et al. (1993) *FEBS Letters* 323:73–76); MPI gene (Corderok et al. (1994) *Plant J.* 6(2):141–150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Tissue-preferred promoters can be utilized to target enhanced SCIP-1 expression within a particular plant tissue.

Tissue-preferred promoters include Yamamoto et al. (1997) *Plant J.* 12(2)255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol Biol.* 23(6):1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat No. 5,563,055, Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P: 175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the SCIP-1 of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

It is recognized that with these nucleotide sequences, antisense constructions, complementary to at least a portion of the messenger RNA (mRNA) for the SCIP-1 sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene.

Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The present invention may be used for transformation of any plant species, including, but not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (Saccharum spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (Lathyrus spp.), and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Preferably, plants of the present invention are crop plants (for example, corn, alfalfa, sunflower, Brassica, soybean, cotton, safflower, peanut, sorghum, wheat, millet, tobacco, etc.). Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The invention is drawn to compositions and methods for increasing the resistance of plant to plant pests. Accordingly, the compositions and methods are also useful in protecting plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened.

By "antipathogenic compositions" is intended that the compositions of the invention have antipathogenic activity and thus are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888–1892, herein incorporated by reference). Additionally, microspectrophotometrical analysis can be used to measure the in vitro antipathogenic properties of a composition (Hu et al. (1997) *Plant Mol. Biol.* 34:949–959 and Cammue et al. (1992) *J. Biol. Chem.* 267: 2228–2233, both of which are herein incorporated by reference).

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium*

(*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora,* Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root-knot, cyst, and lesion nematodes, including Meloidogyne, Heterodera and Globodera spp.; particularly *Meloidogyne incognita, Meloidogyne javanica, Meloidogyne hapla, Meloidogyne chitwoodi, Meloidogyne arenaria, Meloidogyne fallax, Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis,* European corn borer; *Agrotis ipsilon,* black cutworm; *Helicoverpa zea,* corn earworm; *Spodoptera frugiperda,* fall armyworm; *Diatraea grandiosella,* southwestern corn borer; *Elasmopalpus lignosellus,* lesser cornstalk borer; *Diatraea saccharalis,* surgarcane borer; *Diabrotica virgifera,* western corn rootworm; *Diabrotica longicornis barberi,* northern corn rootworm; *Diabrotica undecimpunctata howardi,* southern corn rootworm; *Melanotus* spp., wireworms; *Cyclocephala borealis,* northern masked chafer (white grub); *Cyclocephala immaculata,* southern masked chafer (white grub); *Popillia japonica,* Japanese beetle; *Chaetocnema pulicaria,* corn flea beetle; *Sphenophorus maidis,* maize billbug; *Rhopalosiphum maidis,* corn leaf aphid; *Anuraphis maidiradicis,* corn root aphid; *Blissus leucopterus leucopterus,* chinch bug; *Melanoplus femurrubrum,* redlegged grasshopper; *Melanoplus sanguinipes,* migratory grasshopper; *Hylemya platura,* seedcorn maggot; *Agromyza parvicornis,* corn blot leafminer; *Anaphothrips obscrurus,* grass thrips; *Solenopsis milesta,* thief ant; *Tetranychus urticae,* twospotted spider mite; Sorghum: *Chilo partellus,* sorghum borer; *Spodoptera frugiperda,* fall armyworm; *Helicoverpa zea,* corn earworm; *Elasmopalpus lignosellus,* lesser cornstalk borer; *Feltia subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; Siphaflava, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; zygogramma exclamationis, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; Delia ssp., Root maggots.

The following examples are presented by way of illustration, not by way of limitation.

EXPERIMENTAL

EXAMPLE 1

Isolation of SCIP-1 Orthologs

Previously, the expression of sunflower SCIP-1 gene was shown to be up regulated in sunflower plants following the infection of the plants with the plant pathogen Sclerotinia or following the treatment of the plants with oxalic acid. Thus, SCIP-1 proteins may have an important role in plant defense to stresses, such as pathogen attack. To identify orthologs of sunflower SCIP-1 in other plants, the nucleotide sequence of sunflower SCIP-1 (SEQ ID NO: 15) was used to search EST databases. ESTs encoding SCIP-1 orthologs were identified in soybean, rice, maize, and wheat. Seven full-length cDNA clones were isolated and sequenced. One unique cDNA clone each was isolated from soybean (SEQ ID NO: 1) and rice (SEQ ID NO: 3), two clones were isolated from maize (SEQ ID NOs: 5 and 7), and three clones from wheat (SEQ ID NOs: 9, 11, and 13). The corresponding deduced amino acid sequences of the SCIP-1 orthologs are set forth in SEQ ID NOs: 2, 4, 6, 8, 10, 12, and 14, respectively.

The amino acid sequences of the eight plant SCIP-1 protein were aligned and compared. The results of the comparison of the amino acid sequences of the seven SCIP-1 orthologs to each other and sunflower SCIP-1 indicated that about 50% amino acid residues are identical among the SCIP-1 proteins from soybean, rice, maize, wheat, and sunflower. The evolutionary relatedness of the SCIP-1 proteins was estimated using the PROTDIST method of PHYLIP (Phylogeny Inference package), Version 3.5c (Felsenstein (1993), Department of Genetics, University of Washington, Seattle, distributed by the author, see, evolution.genetics.washington.edu/phylip.html), using default parameters.

The plant SCIP-1 protein sequences were used to search the GenBank database. The search revealed two EST clones from Arabidopsis (Accession Nos. Z17627 and Z17689), one EST clone from soybean (Accession No. A1442274), one EST clone from rice (Accession No. C27062) and one clone from the common ice plant (*Mesembryanthemum crystallinum*) (Accession No. A1032451) that encode putative SCIP-1 orthologs. An alignment of deduced amino acid sequence alignment of the GenBank accessions and five plant SCIP-1 proteins was prepared. The alignment revealed that the ten amino acid sequences are homologous and share several highly conserved domains. Additionally, amino acid sequences from the same species such as, for example, rice SCIP-1 (SEQ ID NO: 3) and rice SCIP-1 EST (Accession No. C27062), have greater sequence similarity than amino acid sequences from different species.

The GenBank database search also revealed that the five plant SCIP-1 proteins share sequence similarity with several bacterial proteins which may be bacterial SCIP-orthologs. The bacterial sequences in the alignment include those from *Archeoglobus fulvidus* (Arch. fulv scip-1, Accession No. AAB89551), *Bacillus subtilis* (Bacillus BSDO26_3, Accession No. BAA11717), *Chlamydia pneumoiae* (Chl. pneum. AE001668_3 Accession No. AAD19015), *Chlamydia trachomatis* (Chl. tracho. AE001344_6, Accession No. AAC68331), *Escherichia coli* (*E. coli* ybcL ECAE160_, Accession No. AAC73646), *Escherichia coli* (*E. coli* (biotin) ECBI, Accession No. AAA23513), *Escherichia coli* (*E. coli* scip-1 homol, Accession No. U39938), *Methanothermus fervidus* (*M. fervidus* scip-1 homologue, Accession No. X78345, *Methanobacterium thermoautotrophicum* (Meth. therm. scip-1 homologue, Accession No. AA84779), *Mycobacterium tuberculosis* (Mycobacterium tub. MTCY270_10, Accession No. CAB08653), *Pyrococcus abyssi* (Pyr. abyssi CNSPAX04_21, Accession No. CAB50064), *Pyrococcus hirikoshii* (Pyr. horik.AP000005_1, Accession No. BAA30372) and *Streptomyces coelicolor* (Streptomyces coel. SCI5_, Accession No. CAB45286). After aligning the five plant SCIP-1 sequences and the bacterial sequences, several conserved peptide domains were observed. The sequence alignments indicate that SCIP-1 represents a conserved and widespread family of genes in bacteria and plants. Across all of the deduced amino acid sequences, about 20% of the amino acids were identical and 35% were either identical or conservative substitutions. While the identification of SCIP-1 genes in animals or fungi has not yet been reported, the conservation of SCIP-1 genes across the wide evolutionary distance between prokaryotes and plants suggest that the likelihood of finding SCIP-1 genes in animals and fungi is high.

Although the function of the plant SCIP-1 proteins has not yet been elucidated, one of the bacterial orthologs from *E. coli* was reported to be involved in biotin synthesis (see PCT patent publication WO 94/080230). Thus, the plant SCIP-1 proteins may be involved in biotin biosynthesis in plants. Furthermore, it is recognized that the SCIP-1 nucleotide sequence of the invention may be used to alter the synthesis and/or accumulation of biotin in a plant.

The plant SCIP-1 proteins of the invention were found to have homology with conserved hypothetical proteins from Chlamydia (Accession No. AAD19015) and Methanobacterium (Accession No. AA84779). The plant SCIP-1 proteins shared about 20% amino acid identity with the Chlamydia and Methanobacterium proteins. At the nucleotide sequence level, the nucleotide sequences of the invention were about 40% identical to the nucleotide sequences encoding the Chlamydia (Accession No. AE001668) and Methanobacterium (Accession No. AE000813) proteins.

EXAMPLE 2

Constitutive Expression of SCIP-1 in Transgenic Arabidopsis Enhances Disease Resistance To test the effect of constitutive expression of SCIP-1 on the disease resistance of a plant, Arabidopsis plants were transformed with a nucleotide construct comprising the sunflower SCIP-1 nucleotide sequence (SEQ ID NO: 15). The nucleotide construct additionally comprised an operably linked SCP 1-omega promoter and an operably linked pinII terminator. The nucleotide construct was introduced into Arabidopsis plants by the vacuum infiltration transformation method of Bechtold et al. ((1993) *C.R. Acad. Sci. III* 316:1194–1199) was employed. $T_1$ progeny were selfed, and the resulting $T_2$ individuals that were positive for the presence of the sunflower SCIP-1 in their genome were used in bioassays as described below.

Bioassays were conducted with the transgenic SCIP-1-positive Arabidopsis plants and untransformed controls to assess the effect of the sunflower SCIP-1 nucleotide sequence under the control of a constitutive promoter on the resistance of the transgenic plants to Sclerotinia. For the bioassay, Arabidopsis plants were inoculated with Sclerotinia mycelium. The mycelium were prepared for inoculating the plants by growing mycelium on ⅛ PDA plates at room temperature (about 20–25° C.) in the dark for three days. To inoculate the Arabidopsis plants, a plug (approximately 3 mm in diameter) containing actively growing mycelium was removed from a plate, applied to a branch of an Arabidopsis plant with the mycelium-side of the plug contacting the plant, and then wrapped with Parafilm. Two stems were inoculated per plant. The inoculated plants were incubated in a growth chamber for three days at 25° C., 80% relative humidity, and a photoperiod of 8 h light/16 h dark. To assess the infection process, lesion sizes were determined three days after inoculation.

Plants ($T_2$) from five SCIP-1-positive transgenic events were assayed of lesion length 3 days after inoculation with Sclerotinia (Table 1). Events 2 and 5 displayed an average lesion length that was significantly smaller than the control plants. Events 1, 3, and 4 displayed larger average lesion lengths than the control. However, this increase in lesion length was not significant. Therefore, the results indicate that a Arabidopsis plant that was transformed sunflower SCIP-1 under the control of a constitutive promoter has increased resistance to plant disease, particularly Sclerotinia. The results also demonstrate that SCIP-1 nucleotide sequences can be used to enhance the disease resistance of plants.

TABLE 1

Effect of Sunflower SCIP-1 on Sclerotinia Infection in Arabidopsis

| Events | Sunflower SCIP-1* | Lesion Length (cm)† | | Lesion Length % Control |
|---|---|---|---|---|
| | | Range | Average | |
| Control@ | – | 7.3–2.7 | 5.10 | 100 |
| 1 | + | 7.5–3.0 | 5.45 | 107 |
| 2 | + | 5.3–0.4 | 3.96 | 78 |
| 3 | + | 7.6–3.7 | 5.91 | 116 |
| 4 | + | 6.9–4.4 | 5.89 | 116 |
| 5 | + | 6.8–0.3 | 3.40 | 67 |

@Non-transformed parent plants
*Non-transformed (–); transformed (+) with sunflower SCIP-1
†Lesion length was determined 72 hours after inoculation.

EXAMPLE 3

Transformation and Regeneration of Transgenic Maize Plants

Immature maize embryos from greenhouse donor plants are bombarded with a plasmid containing a SCIP-1 nucleotide sequence of the invention operably linked to the maize ubi-1 promoter, plus a plasmid containing the selectable marker gene PAT (Wohlleben et al. (1988) *Gene* 70:25–37) that confers resistance to the herbicide Bialaphos. Transformation is performed as follows. Media recipes follow below.
Bombardment and Culture Media Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I H$_2$O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H$_2$O) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H$_2$O after adjusting to pH 5.6); 3.0 g/l Gelrite (added after bringing to volume with D-I H$_2$O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H$_2$O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H$_2$O), sterilized and cooled to 60° C.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a SCIP-1 nucleotide sequence of the invention operably linked to maize ubi-1 promoter is made. This plasmid DNA plus plasmid DNA containing a PAT selectable marker is precipitated onto 1.1 μm (average diameter) tungsten pellets using a CaCl$_2$ precipitation procedure as follows:

100 μl prepared tungsten particles in water
  10 μl (1 μg) DNA in TrisEDTA buffer (1 μg total)
  100 μl 2.5 M CaCl$_2$
  10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for SCIP-1 expression.

EXAMPLE 4

Agrobacterium-mediated Transformation of Maize

For Agrobacterium-mediated transformation of maize with an SCIP-1 nucleotide sequence of the invention, preferably the method of Zhao is employed (U.S. Pat. No. 5,981,840, and PCT patent publication WO98/32326), the contents of which are hereby incorporated by reference. Briefly, immature embryos are isolated from maize and the embryos contacted with a suspension of Agrobacterium, where the bacteria are capable of transferring the SCIP-1 nucleotide sequences of interest to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

EXAMPLE 5

Soybean Embryo Transformation and Regeneration of Transgenic Plants

Soybean embryos are bombarded with a plasmid containing an SCIP-1 nucleotide sequence of the invention, operably linked to a promoter of interest, as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the SCIP-1 nucleotide sequence of the invention, operably linked to a promoter of interest, can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 6

Sunflower Meristem Tissue Transformation and Regeneration of Transgenic Plants

Sunflower meristem tissues are transformed with an expression cassette containing an SCIP-1 nucleotide sequence of the invention, operably linked to a promoter of interest, as follows (see also European Patent Number EP 0 486233, herein incorporated by reference, and Malone-Schoneberg et al. (1994) *Plant Science* 103:199–207). Mature sunflower seed (*Helianthus annuus* L.) are dehulled using a single wheat-head thresher. Seeds are surface sterilized for 30 minutes in a 20% Chlorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al.(1990) *Plant Cell Rep.* 9: 55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15: 473–497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzylaminopurine (BAP), 0.25 mg/l indole-3-acetic acid (IAA), 0.1 mg/l gibberellic acid (GA3), pH 5.6, and 8 g/l Phytagar.

The explants are subjected to microprojectile bombardment prior to Agrobacterium treatment (Bidney et al. (1992) *Plant Mol. Biol.* 18: 301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the SCIP-1 nucleotide sequence of the invention, operably linked to a promoter of interest is introduced into Agrobacterium strain EHA105 via freeze-thawing as described by Holsters et al. (1978) *Mol. Gen. Genet.* 163:181–187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an OD$_{600}$ of about 0.4 to 0.8. The Agrobacterium cells are pelleted and resuspended at a final OD$_{600}$ of 0.5 in an inoculation medium comprised of 12.5 mM MES pH 5.7, 1 gm/l NH$_4$Cl, and 0.3 gm/l MgSO$_4$.

Freshly bombarded explants are placed in an Agrobacterium suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for SCIP-1 mRNA, protein and/or activity levels.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by SCIP-1 expression or activity analysis of leaf extracts while transgenic seeds harvested from NPTII-positive $T_0$ plants are identified by SCIP1 expression and/or activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Chlorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 μm tungsten particles are resuspended in 150 μl absolute ethanol. After sonication, 8 μl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA 105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 μg/l kanamycin is resuspended in an inoculation medium (12.5 mM 2-mM 2-(N-morpholino) ethanesulfonic acid, MES, 1 g/l NH$_4$Cl and 0.3 g/l MgSO$_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 μg/ml cefotaxime). The plantlets are cultured on the medium for about two weeks under 16-hour day and 26° C. incubation conditions.

Explants (around 2 cm long) from two weeks of culture in 374C medium are screened for SCIP-1 mRNA and/or protein expression, or SCIP-1 activity, using assays known in the art. After positive (i.e., for SCIP-1 expression) explants are identified, those shoots that fail to exhibit SCIP-1 expression and/or actitivity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for SCIP-1 expression are grafted to Pioneer hybrid 6440 in vitro-grown sunflower seedling rootstock. The rootstocks are prepared in the following manner. Seeds are dehulled and surface-sterilized for 20 minutes in a 20% Chlorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleotide molecule comprising a nucleotide sequence selected from the group consisting of:
   (a) the nucleotide sequence set forth in SEQ ID NO: 5:
   (b) a nucleotide sequence encoding the amino acid sequence set forth in SEQ ID NO: 6;
   (c) a nucleotide sequence encoding a polypeptide having SCIP-1 biological activity, wherein said nucleotide sequence has at least 95% sequence identity to the nucleotide sequence set forth in SEQ ID NO: 5; and
   an antisense nucleotide sequence corresponding to the nucleotide sequence of (a), (b), or (c).

2. An expression cassette comprising the nucleotide sequence of claim 1, wherein said nucleotide sequence is operably linked to a promoter that drives expression in a plant.

3. The expression cassette of claim 2, wherein said promoter is selected from the group consisting of constitutive, pathogen-inducible, insect-inducible, wound-inducible, tissue-preferred, and developmentally regulated promoters.

4. A transformed plant comprising in its genome at least one stably incorporated nucleotide construct comprising a nucleotide sequence operably linked to a promoter capable of driving gene expression in a plant cell, said nucleotide sequence selected from the group consisting of:
   (a) the nucleotide sequence set forth in SEQ ID NO: 5;
   (b) a nucleotide sequence encoding the amino acid sequence set forth in SEQ ID NO: 6;
   (c) a nucleotide sequence encoding a polypeptide having SCIP-1 biological activity, wherein said nucleotide sequence has at least 95% sequence identity to the nucleotide sequence set forth in SEQ ID NO: 5; and
   an antisense nucleotide sequence corresponding to the nucleotide sequence of (a), (b), or (c).

5. The plant of claim 4, wherein said promoter is selected from the group consisting of constitutive, pathogen-inducible, insect-inducible, wound-inducible, tissue-preferred, and developmentally regulated promoters.

6. The plant of claim 4, wherein said plant has increased resistance to at least one pathogen.

7. The plant of claim 4, wherein said plant is a monocot.

8. The plant of claim 7, wherein said monocot is selected from the group consisting of maize, wheat, rice, sorghum, barley, millet, and rye.

9. The plant of claim 4, wherein said plant is a dicot.

10. The plant of claim 9, wherein said dicot is selected from the group consisting of soybean, Brassica sp. alfalfa, Arabidopsis, safflower, sunflower, cotton, peanut, and potato.

11. Transformed seed of the plant of claim 4.

12. Transformed seed of the plant of claim 5.

13. Transformed seed of the plant of claim 8.

14. Transformed seed of the plant of claim 10.

15. A transformed plant cell comprising in its genome at least one stably incorporated nucleotide construct comprising a nucleotide sequence operably linked to a promoter capable of driving gene expression in a plant cell, said nucleotide sequence selected from the group consisting of:

(a) the nucleotide sequence set forth in SEQ ID NO: 5;

(b) a nucleotide sequence encoding the amino acid sequence set forth in SEQ ID NO: 6;

(c) a nucleotide sequence encoding a polypeptide having SCIP-1 biological activity; wherein said nucleotide sequence has at least 95% sequence identity to the nucleotide sequence set forth in SEQ ID NO: 5; an antisense nucleotide sequence corresponding to the nucleotide sequence of (a), (b), or (c).

16. The plant cell of claim 15, wherein said promoter is selected from the group consisting of constitutive, pathogen-inducible, insect-inducible, wound-inducible, tissue-preferred, and developmentally regulated promoters.

17. A method for increasing the resistance of a plant to a pathogen comprising stably incorporating in the genome of said plant a nucleotide construct comprising a nucleotide sequence operably linked to a promoter capable of driving gene expression in a plant cell, wherein said nucleotide sequence is selected from the group consisting of:

(a) the nucleotide sequence set forth in SEQ ID NO: 5;

(b) a nucleotide sequence encoding the amino acid sequence set forth in SEQ ID NO: 6; and (c) a nucleotide sequence encoding a polypeptide having SCIP-1 biological activity, wherein said nucleotide sequence has at least 95% sequence identity to the nucleotide sequence set forth in SEQ ID NO: 5;

wherein the resistance of said pathogen is increased.

18. The method of claim 17 wherein said promoter is selected from the group consisting of pathogen-inducible, insect-inducible, wound-inducible, constitutive, and tissue-preferred promoters.

19. The method of claim 17, wherein said pathogen is Sclerotinia.

* * * * *

UNITED STATES PATENT AND TRADEMARK OFFICE
CERTIFICATE OF CORRECTION

PATENT NO.    : 6,660,907 B2
DATED         : December 9, 2003
INVENTOR(S)   : Carol A. Hendrick, Xu Hu and Guihua Lu It is certified that error appears in the above-identified patent and that said Letters Patent is hereby corrected as shown below:

Column 56,
Line 16, should read -- wherein the resistance of said plant to said pathogen is increased. --

Signed and Sealed this

Twenty-fourth Day of February, 2004

JON W. DUDAS
*Acting Director of the United States Patent and Trademark Office*